(12) United States Patent
Huwais

(10) Patent No.: US 12,178,448 B2
(45) Date of Patent: Dec. 31, 2024

(54) HOLLOW-POINT CONDENSING-COMPACTION TOOL

(71) Applicant: Huwais IP Holding LLC, Jackson, MI (US)

(72) Inventor: Salah Huwais, Jackson, MI (US)

(73) Assignee: Huwais IP Holding LLC, Jackson, MI (US)

( * ) Notice: Subject to any disclaimer, the term of this patent is extended or adjusted under 35 U.S.C. 154(b) by 505 days.

(21) Appl. No.: 17/602,685

(22) PCT Filed: Apr. 9, 2020

(86) PCT No.: PCT/US2020/027401
§ 371 (c)(1),
(2) Date: Oct. 8, 2021

(87) PCT Pub. No.: WO2020/210442
PCT Pub. Date: Oct. 15, 2020

(65) Prior Publication Data
US 2022/0160371 A1 May 26, 2022

Related U.S. Application Data

(60) Provisional application No. 62/831,303, filed on Apr. 9, 2019.

(51) Int. Cl.
*A61B 17/16* (2006.01)
*A61C 3/02* (2006.01)
*A61C 8/00* (2006.01)

(52) U.S. Cl.
CPC ...... *A61B 17/1615* (2013.01); *A61B 17/1637* (2013.01); *A61B 17/1644* (2013.01);
(Continued)

(58) Field of Classification Search
CPC ............ A61B 17/1615; A61B 17/1637; A61B 17/1644; A61B 17/1655; A61C 3/02; A61C 8/0089
See application file for complete search history.

(56) References Cited

U.S. PATENT DOCUMENTS 4,693,644 A * 9/1987 Takahashi ............... B23B 51/04
408/207
5,078,605 A 1/1992 Sutter et al.
(Continued)

FOREIGN PATENT DOCUMENTS

CN 101415375 A 4/2009
CN 107072699 A 8/2017
(Continued)

*Primary Examiner* — Kevin T Truong
*Assistant Examiner* — Diana Jones
(74) *Attorney, Agent, or Firm* — Endurance Law Group PLC

(57) ABSTRACT

A rotary tool configured for high speed condensing and/or cutting action to form a hole. The tool has a body around which is formed a plurality of flutes. Each flute has a cutting face on one side and a densifying face on the other side. A land between adjacent flutes establishes a substantially margin-less working edge along each cutting face. The working edges are configured to produce osseodensification when the tool is operated in the condensing mode. A cavity is formed inside the body with access through its apical end. A plurality of spurs rim the apical end. Each spur has a grinding edge that is offset from said longitudinal axis in the cutting direction of rotation. Some of the flutes open directly into a gullet formed between adjacent spurs. Some of the flutes open directly into leading flanks that fall away from each grinding edge.

20 Claims, 11 Drawing Sheets

(52) U.S. Cl.
CPC ............ *A61B 17/1655* (2013.01); *A61C 3/02* (2013.01); *A61C 8/0089* (2013.01)

(56) References Cited

U.S. PATENT DOCUMENTS

| | | | |
|---|---|---|---|
| 5,429,504 A * | 7/1995 | Peltier | A61C 8/0089 433/165 |
| 2017/0303935 A1 | 10/2017 | Huwais | |
| 2019/0029695 A1 | 1/2019 | Huwais | |

FOREIGN PATENT DOCUMENTS

| | | | | |
|---|---|---|---|---|
| CN | 108778158 | A | 11/2018 | |
| DE | 202011002653 | U1 | 5/2011 | |
| EP | 0373111 | A2 | 6/1990 | |
| EP | 2399534 | A1 * | 12/2011 | ......... A61B 17/1637 |
| EP | 2712571 | A1 | 4/2014 | |
| GB | 2080711 | A * | 2/1982 | ......... B23B 51/0406 |
| JP | S5748412 | A | 3/1982 | |
| JP | H02195954 | B | 10/1994 | |
| JP | 2018108223 | A | 7/2018 | |
| JP | 2019506928 | B | 10/2021 | |

* cited by examiner

HOLLOW-POINT CONDENSING-COMPACTION TOOL

CROSS REFERENCE TO RELATED APPLICATIONS

This application claims priority to U.S. Provisional Patent Application U.S. 62/831,303 filed on Apr. 9, 2019, the entire disclosure of which is hereby incorporated by reference and relied upon.

BACKGROUND OF THE INVENTION

Field of the Invention

The invention relates generally to tools for preparing a hole to receive a screw-in fixture, and more particularly to rotary tools and methods implemented thereby for expanding a hole in bone to receive an implant or other fixation device.

Description of Related Art

An implant is a medical device manufactured to replace a missing biological structure, to support a damaged biological structure, or to enhance an existing biological structure. Bone implants are implants of the type placed into the bone of a patient. Bone implants may be found throughout the human skeletal system, including dental implants in a jaw bone to replace a lost or damaged tooth, joint implants to replace a damaged joint such as in hips and knees, and reinforcement implants installed to repair fractures and remediate other deficiencies like pedicle screws used in spinal stabilization, to name but a few. The proper placement of an implant often requires expert preparation using precision drills with highly regulated speed to prevent burning and pressure necrosis of the bone.

There are several known ways to expertly form a receiving hole, which hole is also sometimes referred to as an osteotomy. More recently, a novel biomechanical bone preparation technique called "osseodensification" has been pioneered by the Applicant of this invention. The osseodensification technique is based on the preservation of host bone and has gained rapid acceptance in the worldwide dental community. In many medical communities, osseodensification is considered a preferred standard of care. Examples of osseodensification can be seen in U.S. Pat. No. 9,028,253, issued May 12, 2015, and in U.S. Pat. No. 9,326,778, issued May 3, 2016, and PCT Publication No. WO 2015/138842, published Sep. 17, 2015. The entire disclosures of these references are hereby incorporated by reference and relied upon to the extent permitted in each relevant jurisdiction.

Generally stated, osseodensification is a procedure for enlarging an osteotomy using a specially designed, multi-fluted, rotary tool or bur. An example of a suitable rotary tool is described in the above-mentioned U.S. Pat. No. 9,326,778. Rotary tools configured to achieve osseodensification for dental applications are marketed as Densah® Burs under license through Versah, LLC of Jackson, Michigan USA.

Unlike traditional drilling techniques, osseodensification excavates little if any bone tissue while forming a hole suitable to receive a screw-in fixture. Rather, the majority of bone tissue is simultaneously compacted in outwardly expanding directions from the osteotomy and auto-grafted (i.e., directly re-patriated). When rotated at high speed in a reversed, non-cutting direction with steady external irrigation, osseodensification burs form a strong and dense layer of bone tissue along the walls and base of the osteotomy. Dense compacted bone tissue produces stronger purchase for the implant and may facilitate faster healing.

There are many different and specialized techniques in the medical field. Despite the impressive benefits of osseodensification, not all techniques are conducive to the osseodensification. The well-known socket shield technique is an example of a dental procedure that has yet to be adapted for osseodensification. To avoid tissue alterations of the ridge after tooth extraction, the socket shield technique was first introduced in 2010 by Hurzeler. Hurzeler suggested that instead of extracting the whole tooth, the buccal aspect of the root could be left intact to preserve the buccal plate of bone and prevent post extraction resorption, at the same time an immediate implant is placed; this would lead to an optimal stable esthetic result after the final delivery of the restoration. To extract the tooth while keeping the buccal aspect intact, Hurzeler advocated use of a fissure bur to cut the tooth mesiodistally, after which the lingual aspect of the tooth is extracted leaving a socket where the implant is to be placed. In some cases, a bone trephine may be used to take out the remaining root leaving a space to receive an implant. The socket shield technique is not currently considered a widely accepted practice due in part to its reputation as being of limited applicability. Those of skill in the art will welcome advances and improvements that expand the applicability of the socket shield technique.

Osseodensification is a relatively new field. As with any emerging technology, new and improved tools and techniques are required as the technology begins to mature and be perfected. Furthermore, there is a continuing need to improve the efficiency of surgical operations so that they can be performed with greater speed and greater ease. Therefore, any improvements in osseodensification tools and/or techniques that result in wider applicability, greater speed and/or greater ease will be welcomed by the medical and industrial communities.

BRIEF SUMMARY OF THE INVENTION

The invention pertains to a rotary tool that is configured to be turned at high speed in both condensing and cutting rotary directions (e.g., clockwise and counter-clockwise) to accomplish different effects while forming a hole in a host material. The host material can be bone or not bone. The rotary tool comprises a shank that will establish a longitudinal axis of rotation. The shank is an elongated shaft having upper end and lower ends. A body extends axially from the lower end of the shank. The body has an apical end which is remote from the shank. A plurality of flutes are disposed about the body. Each flute has a cutting face on one side thereof defining a cutting rake angle and a densifying face on the other side thereof defining a densifying rake angle. Each flute has an axial length and a radial depth. A land is formed between each adjacent pair of flutes. Each land has a substantially margin-less working edge along the cutting face of one the flute. A cavity is disposed in the body. The cavity extends axially within the body and opens through the apical end. A plurality of spurs are disposed on the apical end of the body. The spurs are located around the opening of the cavity.

The present invention represents an improvement of the rotary tool designed to densify when used in a non-cutting direction (typically the counter-clockwise direction when viewed from the surgeon's perspective), as described in US Publication No. 2019/0029695. The tool can be used in densifying mode with easier application and less vertical force compared with the design of US 2019/0029695. Therefore, this tool can be used in a wider variety of applications, including but not limited to bone preparation applications.

BRIEF DESCRIPTION OF THE SEVERAL VIEWS OF THE DRAWINGS

These and other features and advantages of the present invention will become more readily appreciated when considered in connection with the following detailed description and appended drawings, wherein.

DETAILED DESCRIPTION OF THE INVENTION

The present invention represents an improvement of the rotary tool designed to densify when used in a non-cutting direction, as described in US Publication No. 2019/0029695 to Huwais, published Jan. 31, 2019, the entire disclosure of which is hereby incorporated by reference and relied upon in jurisdictions recognizing the practice.

A tool according to one embodiment of this present invention is generally shown at 20 throughout the Figures. The rotary tool 20, which may be referred to as a bur or osteotome when configured for use in surgical applications, is designed to be turned at high speed in alternative condensing and cutting rotary directions to accomplish different effects in the host material. To be clear, in surgical applications the host material is bone. In other applications, the host material could be wood, plastic, solid metal, foam metal, solid plastic, cellular plastic, and the like. The tool 20 has a shank 22 and a body 24. For convenience and purposes of illustration, references to the surgical application dominate the following descriptions. And in this context, the host material may occasionally be referred to as bone and any hole therein an osteotomy. Despite these application-specific references, it is to be understood that the tool 20 may be used in suitable non-surgical applications.

Figure 1:
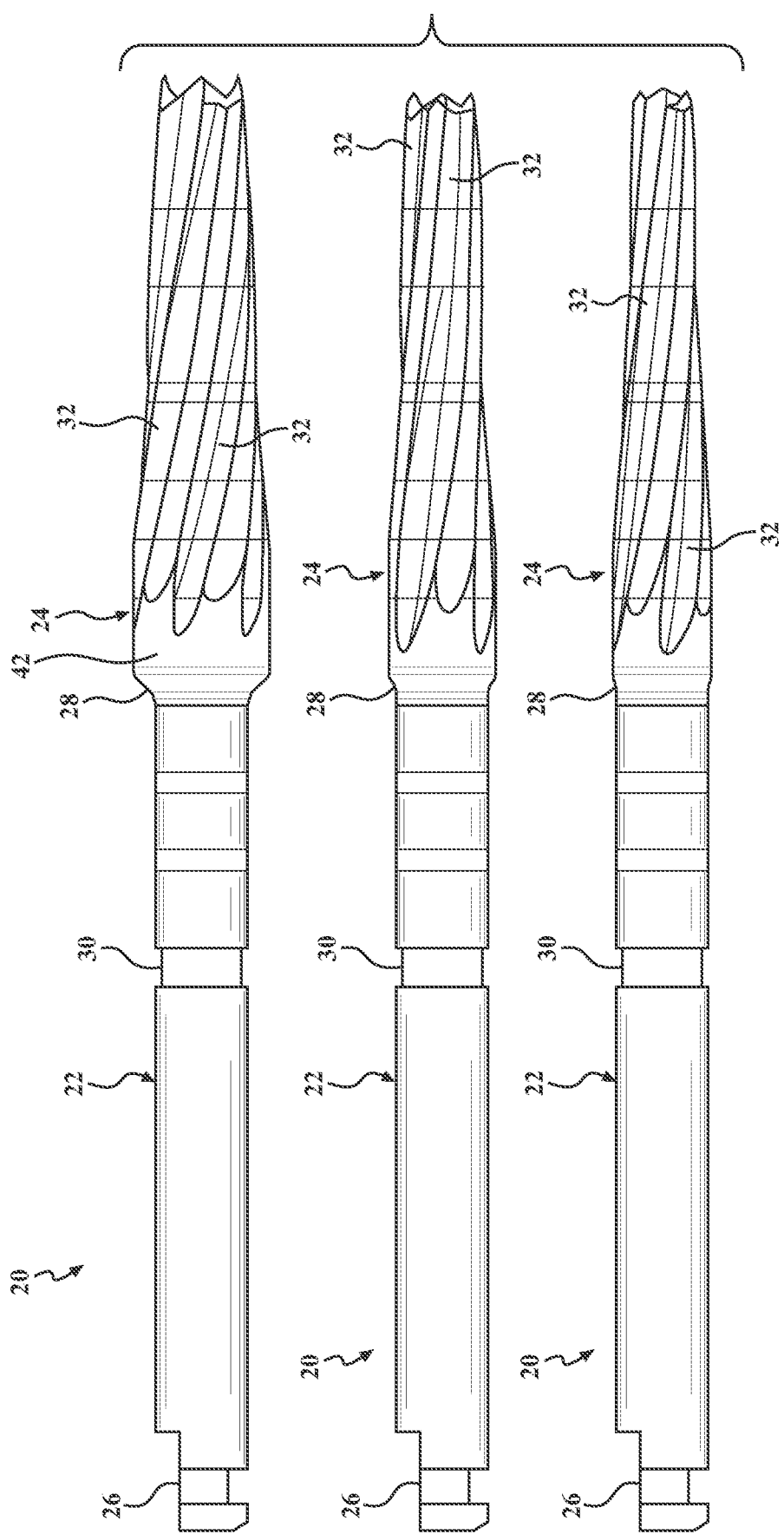
FIG. 1 shows in side elevation a kit of three rotary tools according to one embodiment of the invention, each tool being a different size to enable hole formation in a progressive sequence.
Figure 2:
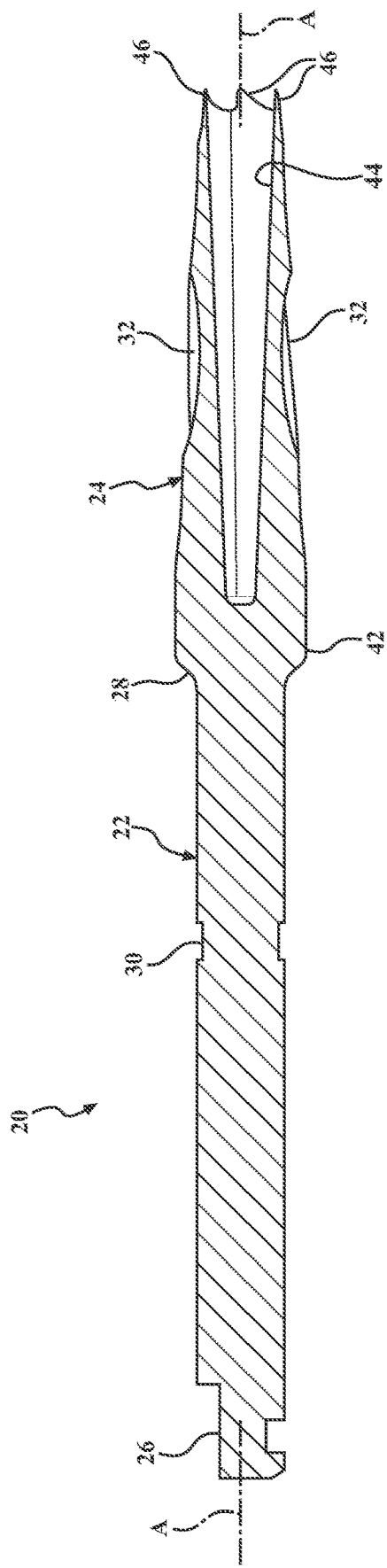
FIG. 2 is a longitudinal cross-section through a rotary tool of the type shown in FIG. 1.
Figure 3:
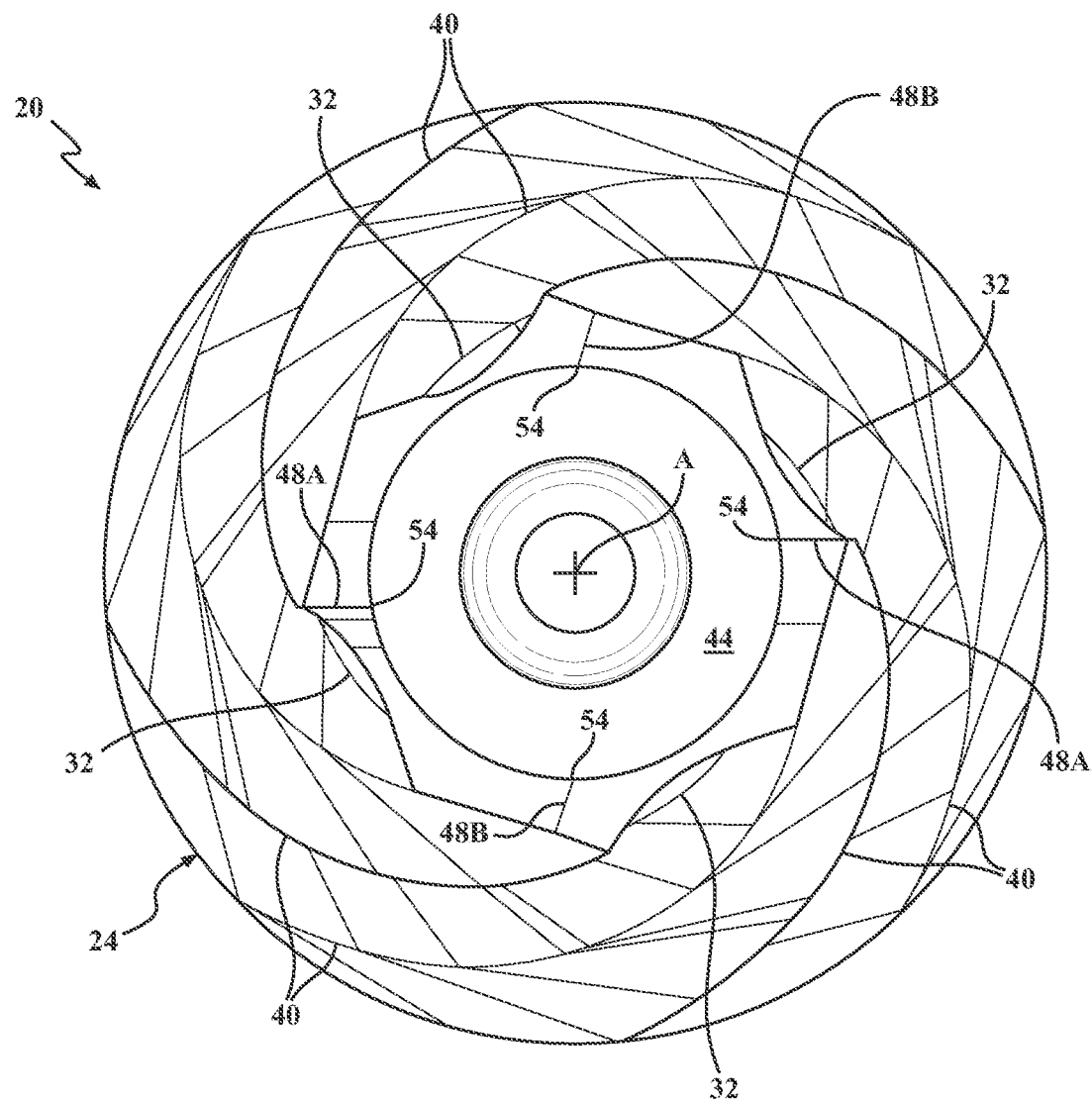
FIG. 3 is an apical end view of a rotary tool of the type shown in FIG. 1.

The shank 22 establishes a longitudinal axis of rotation A for the tool 20. The shank 22 is an elongated shaft, typically (but not necessarily) cylindrical in shape, having an upper end and a lower end. A drill motor engaging interface 26 is formed at the upper end of the shank 22 for connection to a drill motor (not shown). The particular configuration of the interface 26 may vary depending on the type of drill motor used, and in some cases may even be merely a smooth portion of the shank 22 against which the jaws of a collet grip. The body 24 joins to the lower end of the shank 22, which joint may be formed with a tapered or domed transition 28. The transition 28 acts like flow diffuser as the surgeon irrigates with water during a procedure. The gentle transition 28 facilitates the flow of irrigating fluid onto the osteotomy site while the tool 20 is spinning. FIGS. 1 and 2 evidence the inclusion of an optional annular locking notch 30 disposed in the shank 22 between its upper and lower ends. The notch 30 may be used for various purposes, including to couple a depth-stop device like that shown, for example, in WO2018071863A1 to Huwais, published Apr. 19, 2018.

Figure 8:
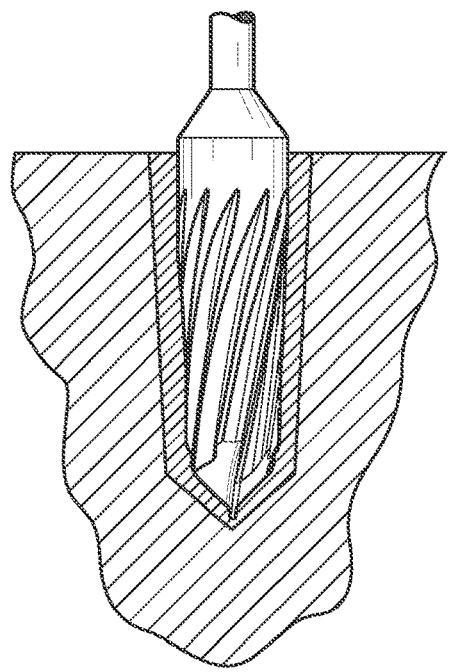
FIG. 8 represents an optional finishing step using a prior art style osseodensification bur after forming a hole as per the example of FIGS. 7A-H.
Figure 9:
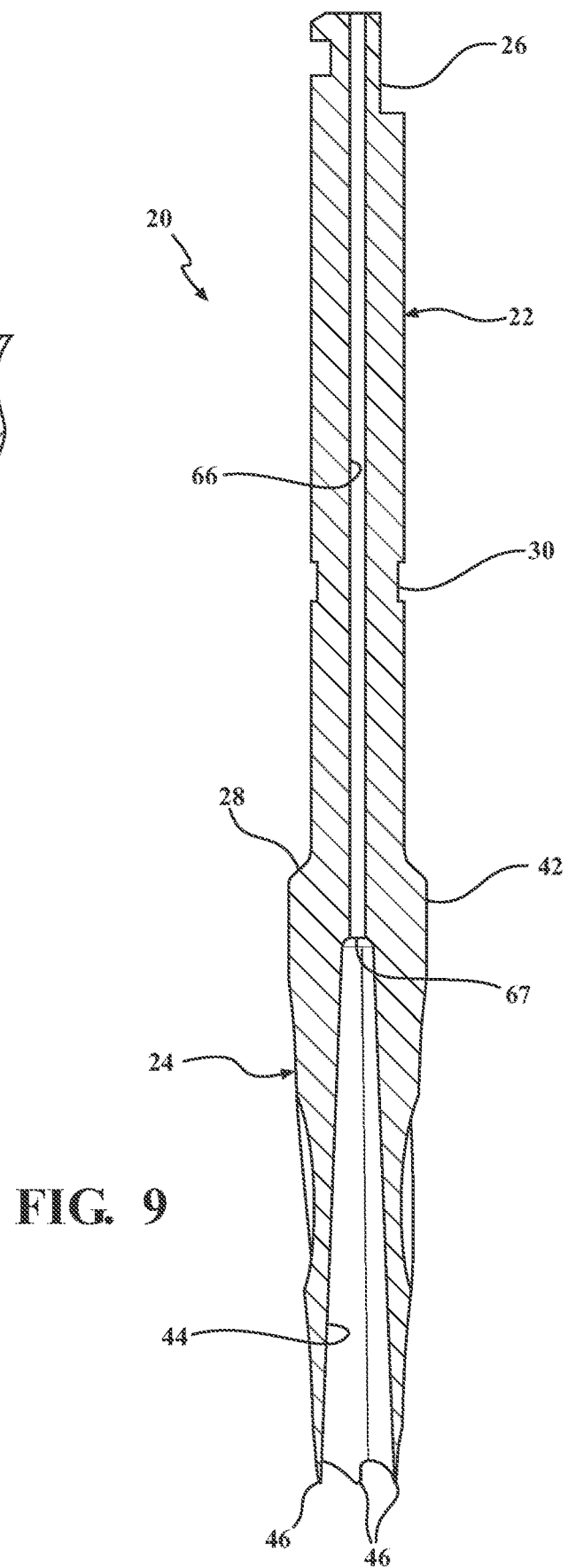
FIG. 9 is a longitudinal cross-sectional view as in FIG. 2 but portraying an alternative embodiment in which an irrigation duct is integrated into the shank of the rotary tool.
Figure 10:
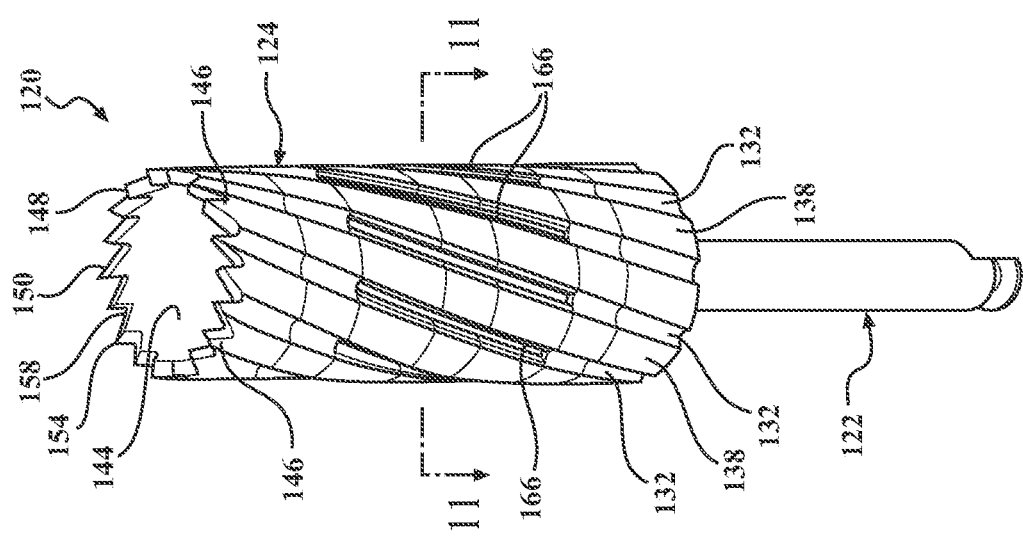
FIG. 10 is a perspective view of a rotary tool according to another embodiment of this invention in which the body is straight-sided (i.e., not tapered) and irrigation ducts are integrated into the body of the rotary tool.

The body 24 extends axially from the lower end of the shank 22. The body 24 has a leading or apical end located remote from the shank 22. In the example of FIGS. 1-9, the body 24 is configured with a conically tapered exterior profile. The outside shape of the body 24 can be seen as decreasing from a maximum diameter adjacent the shank 22 to a minimum diameter adjacent its apical end. However, in some contemplated embodiments the body 124 may be non-tapered (i.e., straight or cylindrical). For example, FIG. 10 shows an example where the body 124 has a generally straight exterior profile that maintain a generally constant diameter along its entire length.

The working length or effective length of the body 24 is proportionally related to its taper angle and to the size and number of tools 20 in a kit. FIG. 1 shows three tools 20, each members of the same kit. Preferably, all tools 20 in a kit will have the same taper angle, or approximately the same taper angle. Taper angles between about 1° and 5° (or more) are possible depending upon the application. More preferably taper angles between about 2°-3° will provide satisfactory results. And still more preferably, a taper angle of about 2° 36'. is known to provide outstanding results for dental applications when the body 24 length is between about 1 mm and 15 mm.

In kit arrangements like that exemplified in FIG. 1, the diameter at the upper end of the body 24 for one tool 20 is approximately equal to the diameter adjacent the apical end of the body 24 for the next larger size tool 20. That is to say, the diameter at the upper end of the body 24 for the lowermost/smallest tool 20 is approximately equal to the diameter adjacent the apical end of the body 24 for the middle tool 20. And then the diameter at the upper end of the body 24 for the middle tool 20 is approximately equal to the diameter adjacent the apical end of the body 24 for the uppermost/largest tool 20. However, these dimensions are only suggested as examples.

A plurality of grooves or flutes 32 are disposed about the body 24. The flutes 32 may or may not have common axial length and common radial depths. That is to say, it is possible that the flutes 32 could, in some configurations, not all be identical. The flutes 32 are preferably, but not necessarily, equally circumferentially arranged about the body 24.

The diameter of the body 24 may influence the number of flutes 32. In the illustrated embodiment, the flutes 32 are formed with a helical twist. If the cutting direction is in the right-hand (clockwise) direction, then preferably the helical spiral is also in the right-hand direction.

Each flute 32 has a cutting face 34 on one side thereof defining a cutting rake angle, and a densifying face 36 on the other side thereof defining a densifying rake angle. That is, each flute 32 has a densifying face 36 and an opposing cutting face 34. A rib or land 38 is formed between adjacent flutes 32, in alternating fashion (i.e., flute-land-flute-land-flute, etc.). Each land 38 bridges the densifying face 36 of the flute 32 on one side to the cutting face 34 of the flute 32 on its other side. The sharp interface between each land 38 and its associated cutting face 34 is referred to as a working edge 40. Depending on the rotational direction of the tool 20, the working edge 40 either functions to cut bone or compact (densify) bone. That is, when the tool 20 is rotated in the cutting direction, the working edges 40 slice and excavate bone (or other host material). When the tool 20 is rotated in the densifying (non-cutting) direction, the working edges 40 compress, compact, and radially displace bone (or other host material) with little-to-no cutting whatsoever. This compaction and radial displacement is exhibited as gentle pushing of the osseous structure laterally outwardly in a condensation, i.e., compaction, mechanism.

The working edges 40 are shown throughout the illustrations as being substantially margin-less. The term margin-less is defined as the entire portion of each land 38 is cut away behind the working edge 40 to provide complete clearance. In standard prior art burs and drills, margins are incorporated behind the cutting edge to help guide the drill in the hole and maintain the drill diameter. In the illustrated examples, the working edge 40 can be seen helically twisting about the body 24. Furthermore, the working edges 40 wind about the body 24 in a direction that turns away from a non-cutting direction. This is perhaps best perceived from the full side views of FIG. 1. As the conically tapered profile decreases in diameter, i.e., moving toward the apical end, the working edges 40 twist about the body 24 in the same direction as the cutting direction.

As mentioned, the cutting face 34 establishes the cutting rake angle for each respective working edge 40. The cutting rake angle can be any one of several forms. In some embodiments the cutting rake angle remains continuously negative angle along its entire length. In some cases, the pitch of the continuously negative cutting rake angle fluctuates along the length of each flute 32 with a total variance of less than 30°. In other cases, the pitch of the continuously negative cutting rake angle may fluctuate with greater than 30° total variance. In those examples where the cutting rake angle fluctuates (and yet remains continuously negative angle along its entire length), changes in pitch along the length of the flute 32 can be progressive or, regressive. A progressive pitch becomes sharper (closer to 90°), whereas a regressive pitch becomes flatter.

Preferably, the densifying rake angle for each working edge 40 will remain continuously negative angle along its entire length. This is to maximus the condensing attributes of the tool 20 when operated in the densifying direction. When the tool 20 is counter-rotated in the densifying mode (i.e., condensing direction per FIG. 4), the densifying rake angle established between the working edge 40 and the land 38 may lie at a large negative angle in the order of about 55°-89°. The large negative densifying rake angle of the working edge 40 (when rotated in a densifying direction) applies outward pressure at the point of contact between the wall of the osteotomy and the working edge 40 to create a compression wave ahead of the point of contact, loosely akin to spreading butter on toast. Osseodensification may also be loosely compared to the well-known process of burnishing metal to improve metal surface quality. The densifying rake angle can any one of several forms. In one embodiment, the densifying rake angle is generally constant along the length of each flute 32. In another embodiment, the densifying rake angle fluctuates along the length of the flutes 32 with a total variance of less than 30°.

These variations in cutting and densifying rake angles can be matched with variations in the length and depth of each flute 32. Each flute 32 has an axial length and a radial depth. The smooth, non-fluted portion of the body adjacent the domed transition 28 is referred to as a stopper section 42. The stopper 42 is that section of the body 24 disposed between the flutes 32 and the shank 22. In cutting mode, once the stopper section 42 enters an osteotomy all excavated bone debris becomes trapped in the flutes 32, which enables some advantageous compaction activity.

The axial lengths of the flutes 32 are shown in the drawings to be generally equal, however other options are available. For example, the axial length of one or some flutes 32 (e.g., every other flute 32) could be shortened to provide certain effects. The radial depth of the flutes 32 are also subject to modest manipulation. In one example. The radial depth of each flute 32 remains generally constant along its length. In another example, the radial depth of each flute 32 has a regressive characteristic, in that the depth measure adjacent the apical end is largest moving progressively shallower toward the stopper section 42.

In the condensing/densifying mode, downward pressure applied by the surgeon is needed to keep the working edges 40 in contact with the bone surface of the osteotomy as it is being expanded. That is, pressure is needed to generate and propagate a compression wave in the host material that begins when the contact stresses exceed the yield strength of the host material. This is aided by the taper effect of the osteotomy and tool 20 to create lateral pressure (i.e., in the intended direction of expansion). The harder the surgeon pushes the tool 20 into the osteotomy, the more pressure is exerted laterally. This gives the surgeon complete control of the expansion rate irrespective to a large degree on the rotation speed of the tool 20, which is a factor underlying the short learning curve required to master the osseodensification technique. Thus, the intensity of the compaction effect depends chiefly on the amount of force exerted on the tool 20, which is controlled by the surgeon. The more force exerted; the quicker expansion will occur.

In the condensing/densifying mode, as each working edge 40 wipes across the bone, the applied forces can be decomposed into two components: one normal to the bone surface, pressing it outwardly, and the other tangential, dragging or smearing it along the inner surface of the osteotomy. As the tangential component is increased, the working edge 40 will start to slide along the bone. At the same time, the normal force will deform the softer bone material. If the normal force is low, the working edges 40 will rub against the bone but not permanently alter its surface. The rubbing action will create friction and heat, but this can be controlled by the surgeon by altering, on-the-fly, the rotation speed and/or pressure and/or irrigation flow. Because the body 24 of the tool 20 is tapered, the surgeon may at any instant during the surgical procedure lift the working edges 40 away from contact with the surface of the bone to allow cooling. This can be done in a controlled "bouncing" fashion where pressure is applied in short bursts with the surgeon continuously monitoring progress and making fine corrections and adjustments.

A distinguishing characteristic of the tool 20 as compared to that described in US 2019/0029695 is a cavity 44 disposed in the body 24 and passing through its apical end. That is, the cavity 44 extends axially within the body 24 and opens at the apical end, creating the appearance of a hollow point. The presence of the cavity 44 removes a substantial portion of the formations at the apical end, leaving only the radially outermost features. The cavity 44 extends into the body 24 of the tool 20 about as deep as the flutes 32 extend along the exterior surface. That is to say, the cavity 44 and the exterior flutes 32 are generally/approximately co-extensive, with both terminating near the conical transition region of the body 24 below the tool shank 22. However, this is subject to variation, it being contemplated that in some cases the cavity 44 may have a short axial length than the axial length of the flutes 32, or alternatively may have a longer axial length than the axial length of the flutes 32 along the exterior surface of the body 24.

As perhaps best seen in FIG. 2, the cavity 44 may have a frusto-conical profile. Its conical shape being widest adjacent the apical end and narrowest adjacent the shank 22. In this sense, the frusto-conical profile can be considered the negative or opposite of the tapered exterior profile of the body 24. In some embodiments, it has been found advantageous to form the frusto-conical taper angle of the cavity 44 generally equal, albeit negative, to the conically tapered exterior profile of the body 24. That is, the cavity 44 may be formed with a frusto-conical taper that matches, or generally approximates, the exterior taper angle of the working end of the tool 20. However, this is only a general preference. In other embodiments, the frusto-conical taper angle of the cavity 44 is not matched to the conically tapered exterior profile of the body 24. Indeed, straight side wall exteriors as well as cavities are entirely possible and, in some cases, may even be preferred. See for example the embodiment of FIGS. 10 and 11.

Figure 5:
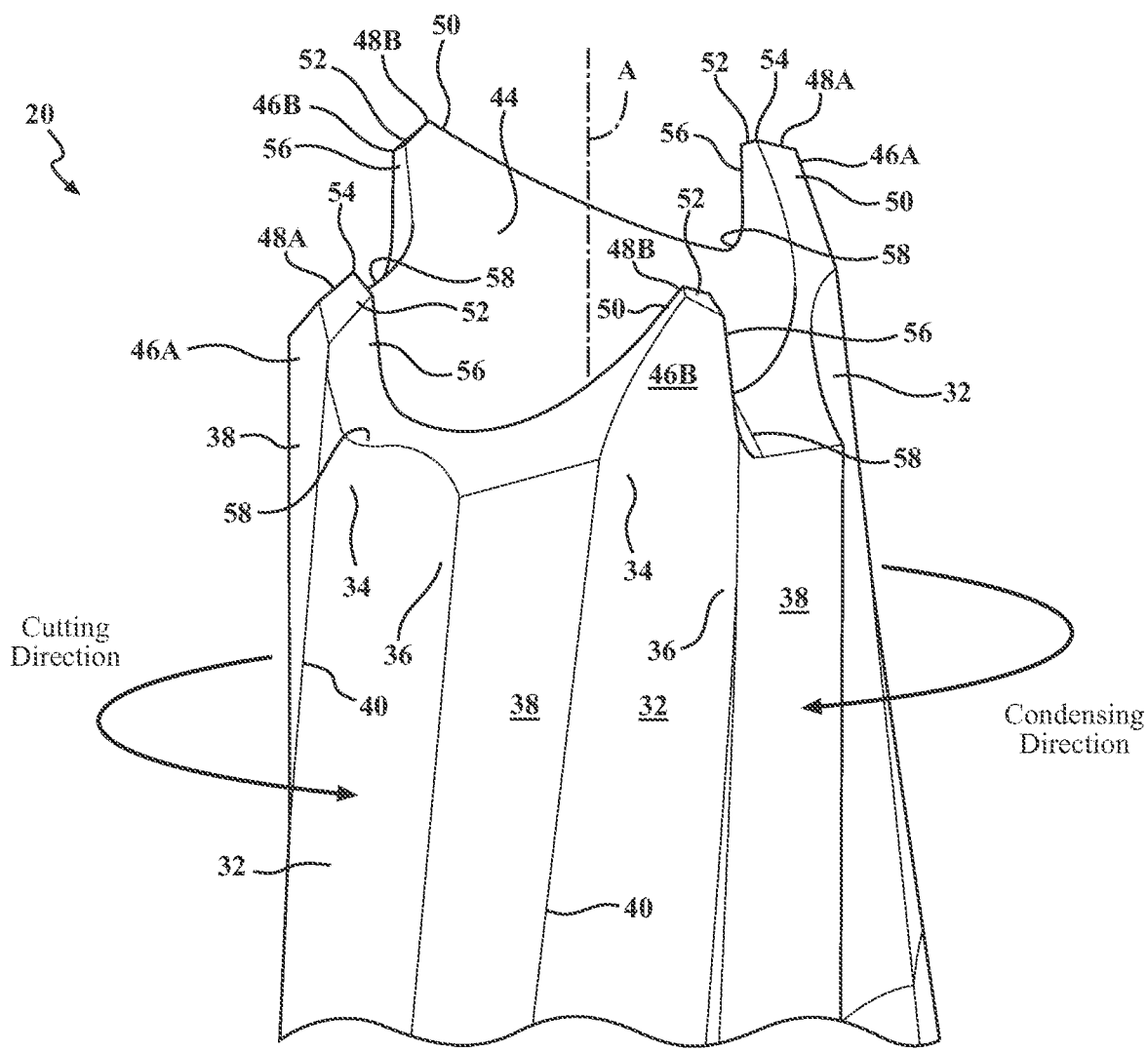
FIG. 5 is a fragmentary perspective view of the apical end of a rotary tool of the type shown in FIG. 1.
Figure 6:
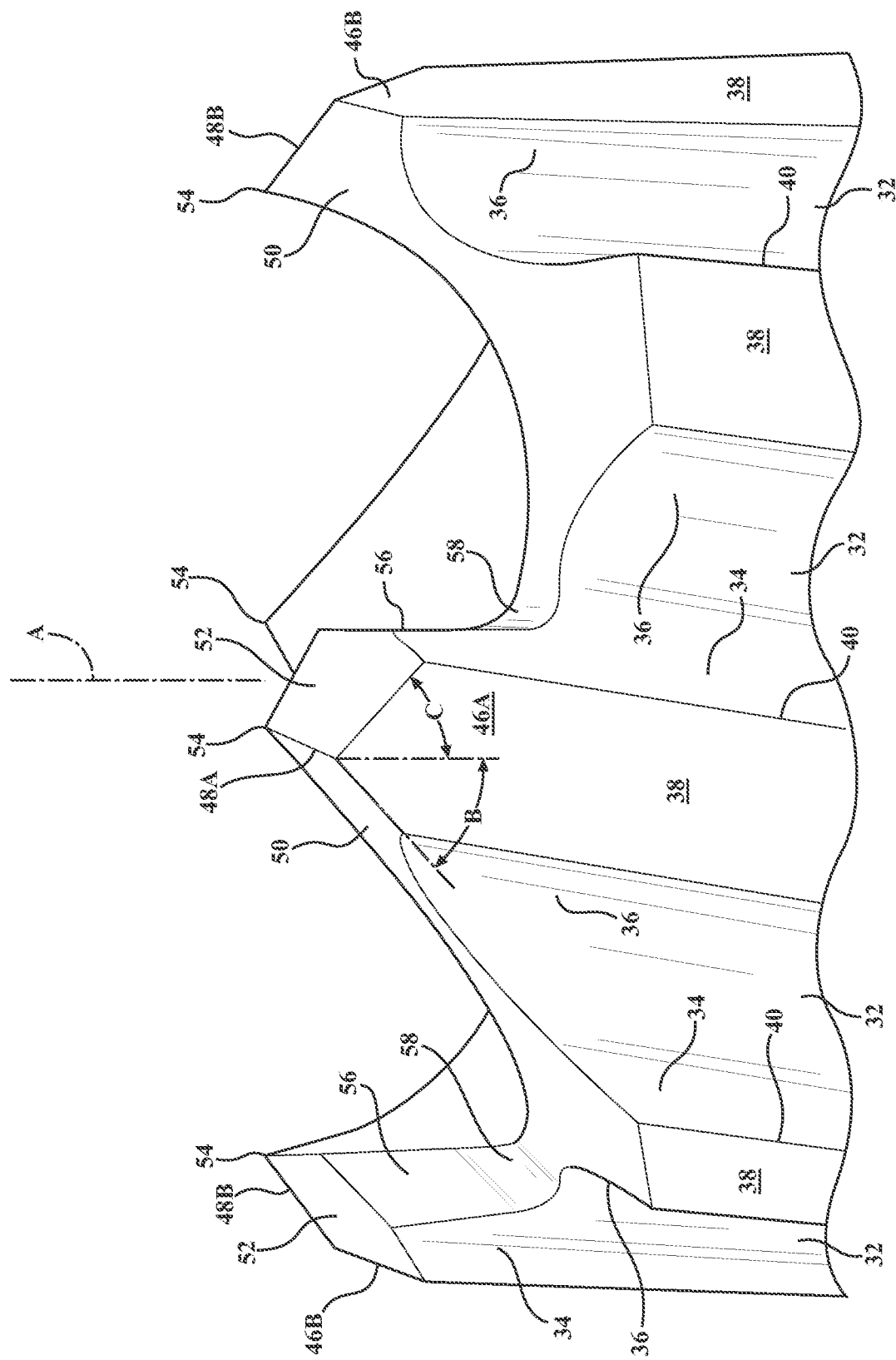
FIG. 6 is a highly magnified perspective view of the apical end of a rotary tool of the type shown in FIG. 5.

FIGS. 5 and 6 offer enlarged views of the apical end, which is also distinguished in configuration from the aforementioned US 2019/0029695 by a plurality of spurs 46 disposed on the apical end of the body 24. The spurs 46 are arranged around the opening of the cavity 44. While four spurs 46 are shown in these examples, it is contemplated that a tool 20 could have fewer or more spurs 46. In particular, smaller diameter burs 20 might have just two or three spurs 46, whereas larger burs might have six or eight or any suitable number of spurs 46.

Each spur 46 has a grinding edge 48 in the shape of a ridgeline. On one side of each grinding edge 48 is a leading flank 50, and on the other side is a trailing flank 52. The terms "leading" and "trailing" are in reference to the non-cutting condensing direction which is indicated in FIG. 5. (Naturally, when the tool 20 is rotated in the cutting direction, these "leading" and "trailing" designations will be antithetical.) Thus, each spur 46 has a grinding edge 48 that forms the ridgeline between leading 50 and trailing 52 flanks.

The included angle between the leading 50 and trailing 52 flanks (B+C in FIG. 6) may be between about 45-135 degrees. In the illustrated examples, the included angle (B+C) at the grinding edge 48 is between about 90-100 degrees and is generally equally set so that each flank 30, 32 angles away from a normal (perpendicular) plane about (but not necessarily exactly) the same degree. That is to say, in the illustrated embodiments, B≈C. In an example where the included angle at the grinding edge 48 is exactly 90 degrees, each of its flanks 30, 32 will be canted at about 45 degrees relative to the horizontal surface. (B=C=45°.) In this configuration, i.e., where each flank 30, 32 angles away from a normal plane about the same degree, the grinding edge 48 will form the same negative rake angle regardless of whether the tool 20 is rotated in a cutting or non-cutting condensing direction. However, this is not necessarily the case; in some contemplated examples B≠C. It may, for example, be desirable to establish a larger rake angle in condensing mode than in cutting mode (B>C), or vise versa (B<C).

FIGS. 1-6 illustrate contemplated configurations where the flanks 50, 52 are each angled so that the resulting grinding edges 48 are also angled thereby forming an apex 54 at the radially inward most end of each grinding edge 48, adjacent the cavity 44. Furthermore, the manufacturing is carried out in such a way that each apex 54 is disposed in a common plane that perpendicularly bisects the longitudinal axis. That is to say, if the tool 20 were placed apical end down on a flat surface, all of the apexes 54 would make point-contact with the horizontal surface at the same time. In another contemplated embodiment, which is not illustrated, the flanks 50, 52 are formed so that placement of the tool 20 apical end down on a flat surface will result in only one or some of the apexes 54 making point-contact with the horizontal surface while the remaining apexes 54 hover above the flat surface.

In yet another contemplated embodiment, which is not illustrated, the resulting grinding edges 48 are angled so as to form apexes 54 at the radially outward most end of each grinding edge 48, spaced away from the cavity 44. In this configuration, each apex 54 could either lay in a common plane that perpendicularly bisects the longitudinal axis, or alternatively only one or some of the apexes 54 lay in a common perpendicular plane.

In a still further contemplated embodiment, which is not illustrated, the flanks 50, 52 may be ground so that the resulting grinding edges 48 all lay in a common plane that perpendicularly bisects the longitudinal axis. In this variation, there would be no point-like apex. When the tool 20 is stood point-down on a flat surface, its grinding edges 48 will either be in line contact with the horizontal surface or hover parallel above the surface.

All of these variations are considered viable alternatives having beneficial application in different scenarios.

Referring still to FIGS. 5 and 6, it can be seen that each trailing flank 52 is abruptly truncated by a steep face 56. The steep faces 56 each lay in a plane that is parallel to, or nearly parallel to, the longitudinal rotary axis A of the tool 20. Each steep face 56 can be observed intersecting the leading flank 50 of the next adjacent the spur 46, to form a gullet 58 therebetween. Said another way, the steep face 56 of one spur 46 merges with the long sloping leading flank 50 of the next adjacent spur 46 at a gullet 58. Thus, a gullet 58 exists between each spur 46. And by corollary, the number of gullets 58 equals the number of spurs 46. A tool 20 with four spurs 46 will have four gullets 58; a tool 20 with six spurs 46 will have six gullets 58; and so forth. When the tool 20 is used in the cutting direction, the gullets 58 will collect bone debris.

And preferably, at least some of the flutes 32 will be positioned so as to open directly into a respective gullet 58. In an eight fluted tool 20 having four spurs 46 and four gullets 58, one, two, three or four flutes 32 will open directly into a respective gullet 58. It is acceptable for the tool 20 to have more gullets 58 than flutes 38 (as in the example of FIG. 10), so long as at least one flute 38 opens directly into one gullet 58. Also, it is preferable that at least one flute 32 opens directly onto a leading flank 50. A flute 32 opening onto a leading flank 50 can be either just behind the associated grinding edge 48 (as visible in FIG. 6) or partially overlapping the grinding edge 48 (as visible in FIG. 5). In the examples of FIGS. 3-6, the tool 20 is fashioned with eight flutes 32 and four spurs 46/gullets 58. Every other flute 32 opens into a respective gullet 58, whereas the intervening flutes 32 each intersecting a respective leading flank 50 just behind a grinding edge 48. In this manner, bone debris is directly and efficiently channeled up the flutes 32 regardless of whether the tool 20 is used in the cutting direction or in the non-cutting condensing direction.

When the tool 20 is used in the non-cutting condensing direction, bone debris is ground by the grinding edges 48 and pushed along the long leading flanks 50 directly into the waiting flutes 32 that open into the respective leading flanks 50 near a grinding edge 48. And when the tool 20 is used in the cutting direction, bone debris is ground in larger quantities by the grinding edges 48 and pushed along the short trailing flanks 30 into the gullets 58, which in turn feed into the flutes 32 associated therewith. There is therefore benefit in coordinating the number of spurs 46 as a whole-number multiple of the number of flutes 32. A four-flute 32 tool 20 may be optimized with either four or two spurs 46. An eight-flute 32 tool 20 may be optimized with two, four or eight spurs 46. A six-flute 32 tool 20 may be optimized with three or six spurs 46. A twelve-flute 32 tool 20 may be optimized with two, three, four, six or twelve spurs 46. And so forth.

The spurs 46 may be identical to one another or of two or more different styles. The illustrated examples depict spurs 46 of two different styles set in alternating pattern: close-offset spurs 46A and far-offset spurs 46B. In these examples, at least one spur is a close-offset spur 46A and/or at least one spur is a far-offset spur 46B. The suffix "A" here denotes features of the close-offset spurs 46A, whereas suffix "B" denotes features of the far-offset spurs 46B.

Figure 4:
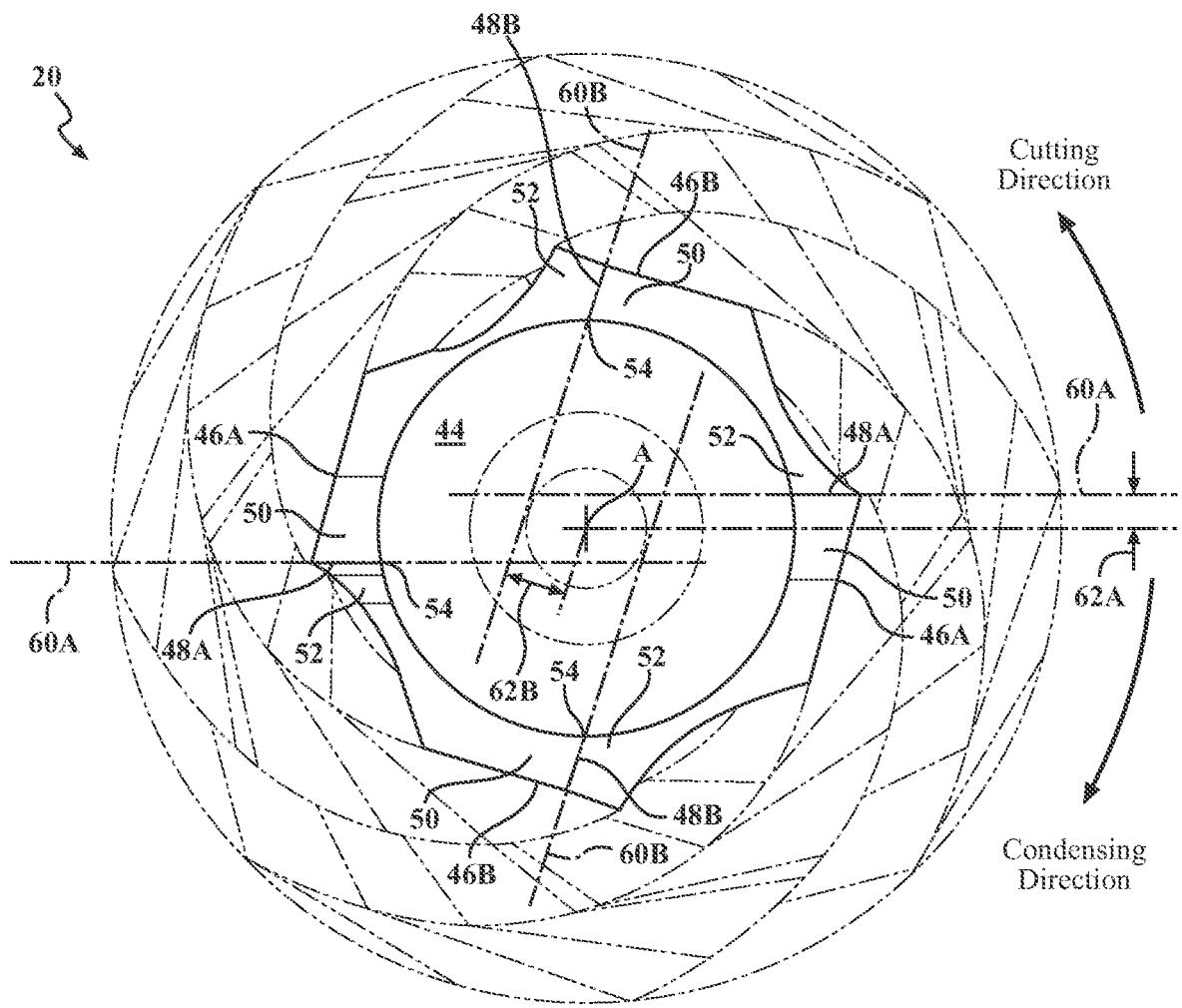
FIG. 4 is a view as in FIG. 3 but emphasizing the apical end in which spur formations can be identified as having close-offset and far-offset qualities.

As perhaps best shown in FIG. 4, the grinding edges 48A of the close-offset spurs 46A are indicated by extension lines 60A. From these extension lines 60A, it can be seen that each grinding edge 48A is offset a short distance 62A from the longitudinal axis of rotation A of the tool 20. Consequently, none of the grinding edges 48A lay along radials from the longitudinal axis of rotation A. Also, it is noteworthy that the offset 62A is in the cutting direction, which will result in a more aggressive grinding action when the tool 20 used in the cutting direction, and a less-aggressive grinding action when the tool 20 is used in the condensing action. Still considering FIG. 4, the grinding edges 48B of the far-offset spurs 46B are indicated by extension lines 60B. From these extension lines 60B, it can be seen that each grinding edge 48B is offset a relatively large distance 62B from the longitudinal axis of rotation A of the tool 20. Consequently, none of the grinding edges 48B lay along radials from the longitudinal axis of rotation A. As in the case of the close-offset spurs 46A, the offset 62B is also in the cutting direction. This difference in offsets 62A:62B is optional and considered generally helpful to enhance the aggressiveness of cutting action. For instance, with none of the grinding edges 48A/B laying along radials from the longitudinal axis of rotation A, and offset in the cutting direction, particles of host material ground and/or displaced by the grinding edges 48A/B will be directed into the surrounding host material with a wiping action. That is to say, the offset grinding edges 48A/B will further contribute to, and even enhance, the autografting function of the tool 20. However, the invention also contemplates and fully embraces an apical end in which the grinding edges 48 all share a common offset distance 62 as well as grinding edges 48 radially arranged from the longitudinal axis of rotation A.

In the dentistry example, an osteotomy is required to receive a bone implant. As previously made clear this invention is not limited to dental applications but may be applied across a wide spectrum of applications. Human (orthopedic) applications are typical, but animal applications are equally plausible and fully within the scope of this invention. Furthermore, the invention is not limited to bone applications, but may be used to prepare holes in non-organic materials for industrial and commercial applications, including but not limited to wood, metal foam plastics and other materials both solid and cellular alike.

Figure 7A:
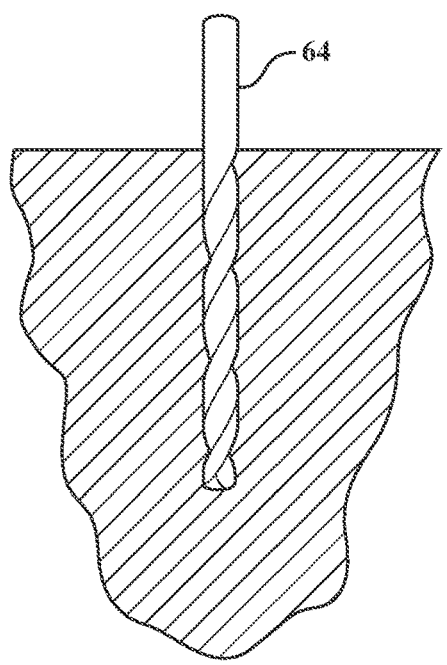
FIGS. 7A-H describe a sequential operation in which a pilot drill forms a pilot hole which is then expanded using progressively larger rotary tools of the type shown in FIG. 1.
Figure 7B:
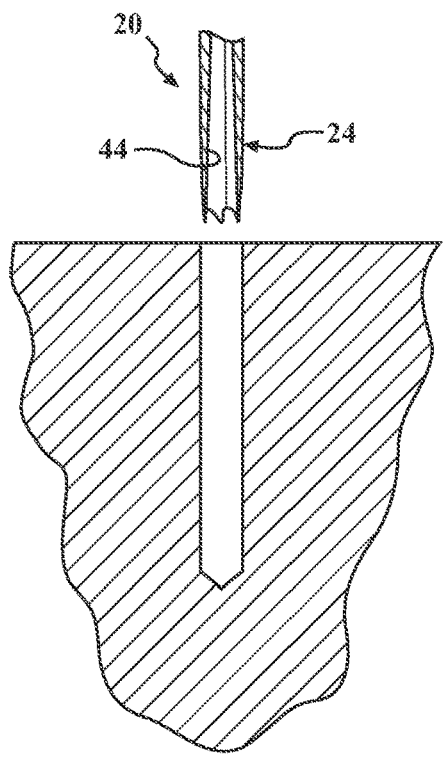
Figure 7C:
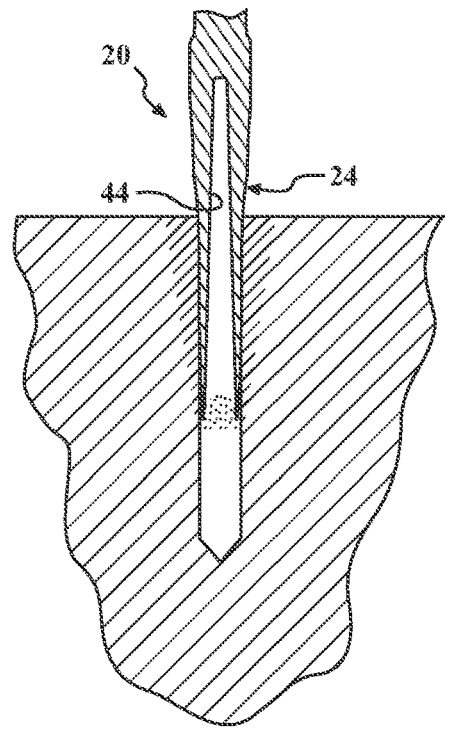
Figure 7D:
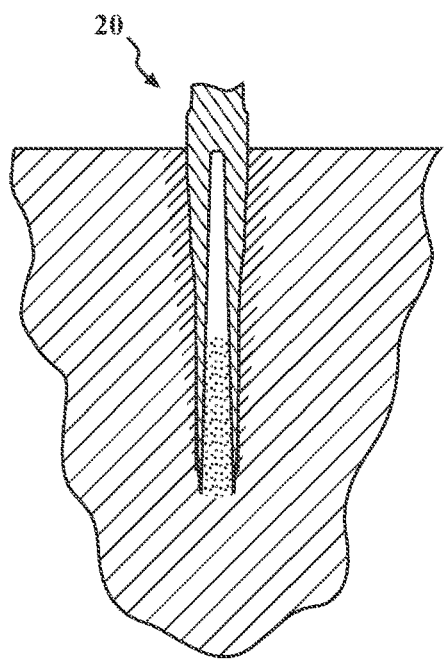

A series of steps are required to accomplish the fully formed osteotomy. In some procedures, the series of steps include first boring a pilot hole (FIG. 7A) into the recipient bone to form the initial osteotomy, and then incrementally expanding the osteotomy using progressively wider bur devices or tools 20, as shown in FIGS. 7B-8, until a final intended diameter is achieved. Once the osteotomy has been prepared, the implant or fixture (not shown) is screwed into place. The procedure of forming an osteotomy is described, generally, below.

In other procedures, such as the previously-described socket shield technique, the series of steps include first extracting a portion of a tooth to form the initial osteotomy, then incrementally expanding the osteotomy using progressively wider bur devices or tools 20 until a final intended diameter is achieved. Once the osteotomy has been prepared, the implant or fixture is screwed into place.

However, the invention is not limited to socket shield procedures. In some applications, it will be desirable to use the improved tool 20, such as in certain hard bone and socket shield conditions. Referring again to FIGS. 7C-H, it can be observed that while the tool 20 continues to provide much the same osseodensification attributes known from US 2019/0029695, the hollow point configuration allows a small quantity of bone debris to collect inside the cavity 44. This can be beneficial for many reasons, including a desire to limit or subdue expansion, or to facilitate penetration when the host material is especially hard.

Figure 11:
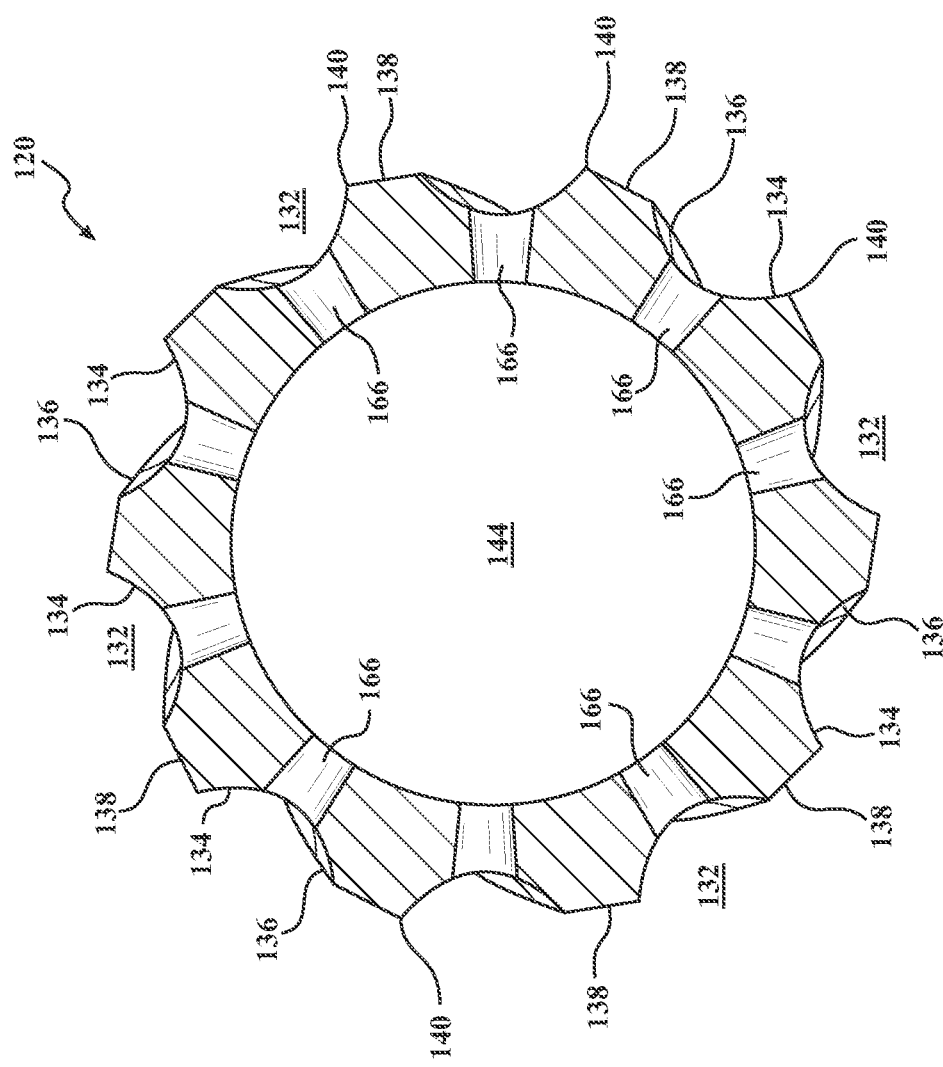
FIG. 11 is a cross-section taken generally along lines 11-11 in FIG. 10.

The Figures do not show the concurrent application of irrigating fluid which is typical in procedures using the tool 20. In normal circumstances, the irrigating fluid will wash into the cavity 44 and help flush out the bone debris to be immediately re-patriated/auto-grafted into the side walls of the osteotomy according to the known principles of osseodensification. FIGS. 9-11 show alternative embodiments in which irrigation ducts may be integrated into the rotary tool 20.

Osseodensification is a method to preserve bone and its collagen content. Osseodensification is effective because it enhances the plasticity of the host material. Osseodensification allows for enlarging an osteotomy by compacting (and/or by cutting when rotation is reversed) with a bur tool 20 in preparation for a subsequently placed implant or fixture. The basic steps of the method begin with the provision of a host material, which in the illustrated embodiment is bone however in other contemplated applications could a non-bone material. A precursor hole is also created in the host material as depicted in FIG. 7A. This precursor hole may be a pilot hole drilled with a relatively small diameter standard twist drill 64 or a hole formed by other methods. In any case, the precursor hole has an interior surface (i.e., sidewall) that extends between a generally circular entrance in an exposed surface of the host material and a bottom that is closed, most commonly by the host material itself. The bottom of the precursor hole may have a generally conical shape as created by the tip of the pilot drill 64.

The method further includes the step of providing a tool 20 configured to be turned at high speed in either a cutting or densifying direction. Whether the tool 20 is enlarging by compacting or by cutting, it rotates at high speed as opposed to low-speed oscillating/rocking motions as taught by some prior art systems. To achieve high speed rotation, the tool 20 is operatively connected to a surgical motor, with its rotation speed set somewhere between about 200-2000 RPM. For dental applications, the torque setting may be about 5-80 Ncm. (Possibly higher for general orthopedic and non-medical/industrial applications.) During the procedure, copious irrigation is provided in the form of a continuous stream of a substantially incompressible liquid (e.g., saline) onto the rotating body 24 adjacent the entrance to the precursor hole as suggested in FIG. 7B.

Returning to FIG. 7C, the body 24 of the tool 20 is continuously rotated in a densifying direction while its apical tip is forcibly advanced into the entrance of the precursor hole. Continued advance results in an enlargement of the precursor hole as shown in FIG. 7D. The rotating body 24 has been by forcibly pushed so that its working edges 40 sweep against the interior surface of the precursor hole to gently expand the bone by incremental plastic deformations that cause a progressive enlargement of the precursor hole beginning adjacent the entrance and developing in a frusto-conical pattern downwardly toward the bottom of the hole. This enlarging step preferably includes axially stroking or pumping the rotating body 24 within the precursor hole so that the working edges 40 alternately lap against the bone interior surface with downward motion and then separate from the interior surface with upward motion in ever deepening movements that cause a progressive plastic deformation of the interior surface of the precursor hole. When the working edges 40 are in physical contact with the bone or dentin (tooth), the surgeon can manually apply variable axial pressure depending on the haptic sensed responsiveness of the bone. The enlarging step also includes lapping the working edges 40 against the interior surface of the precursor hole without the working edges 40 cutting into the surrounding bone, and in a manner where the rate of advance toward the bottom of the precursor hole is independent of the rate of rotation of the body 24. This latter characteristic contrasts with some prior art systems that couple tool rotation with the rate of advance.

Figure 7E:
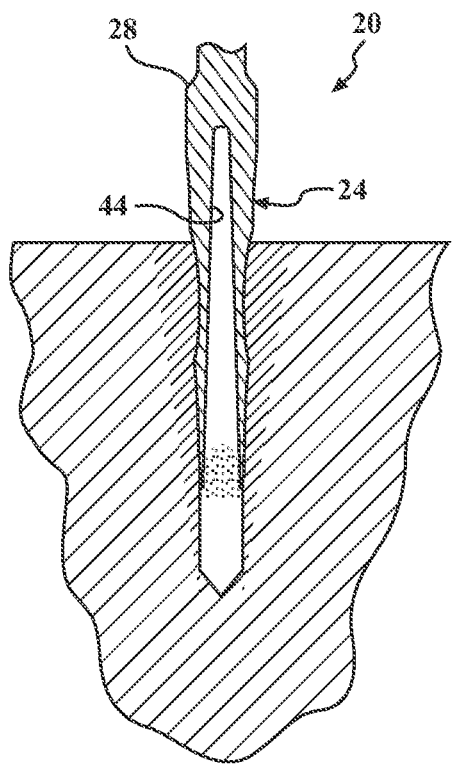
Figure 7F:
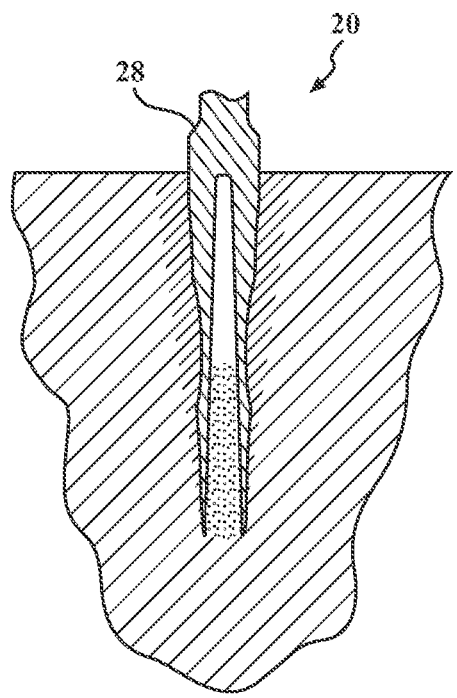
Figure 7G:
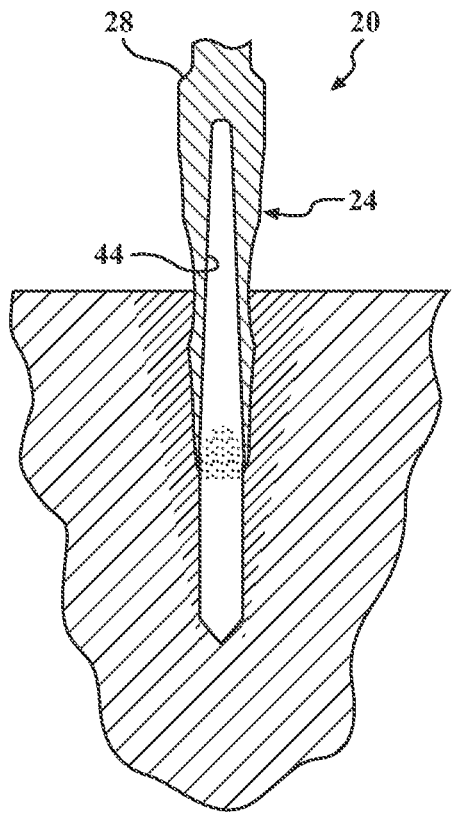
Figure 7H:
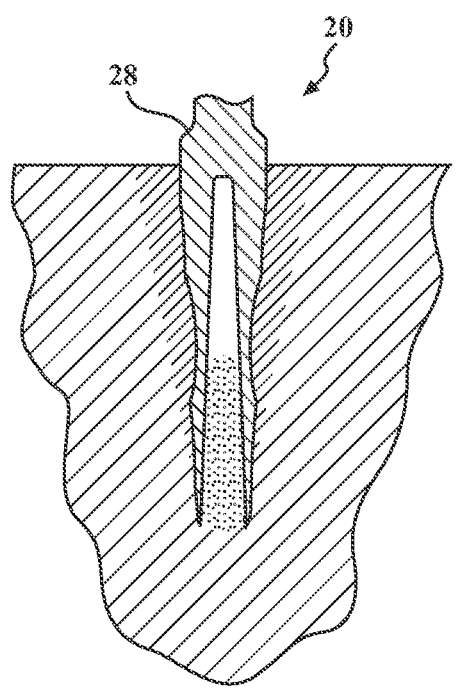

FIGS. 7E and 7F show of the osteotomy using a slightly larger tool 20. Whether this further enlargement is required will be dictated by the specific protocol on a case-by-case basis. If even greater enlargement is needed, a still larger tool 20 can be used to expand the osteotomy, as illustrated in FIGS. 7G and 7H. Indeed, the number of expansion steps required to achieve the correct size osteotomy is dictated by the implant to be placed and the conditions of the host material.

As shown in FIG. 8, if desired, the surgeon may choose a traditional osseodensification tool like that shown in US 2019/0029695 to perform the final expansion/densification step. This will assure that all remaining bone debris in the osteotomy is re-patriated/auto-grafted directly into the side walls of the osteotomy in preparation to receive an implant or anchor.

Figure 9A:
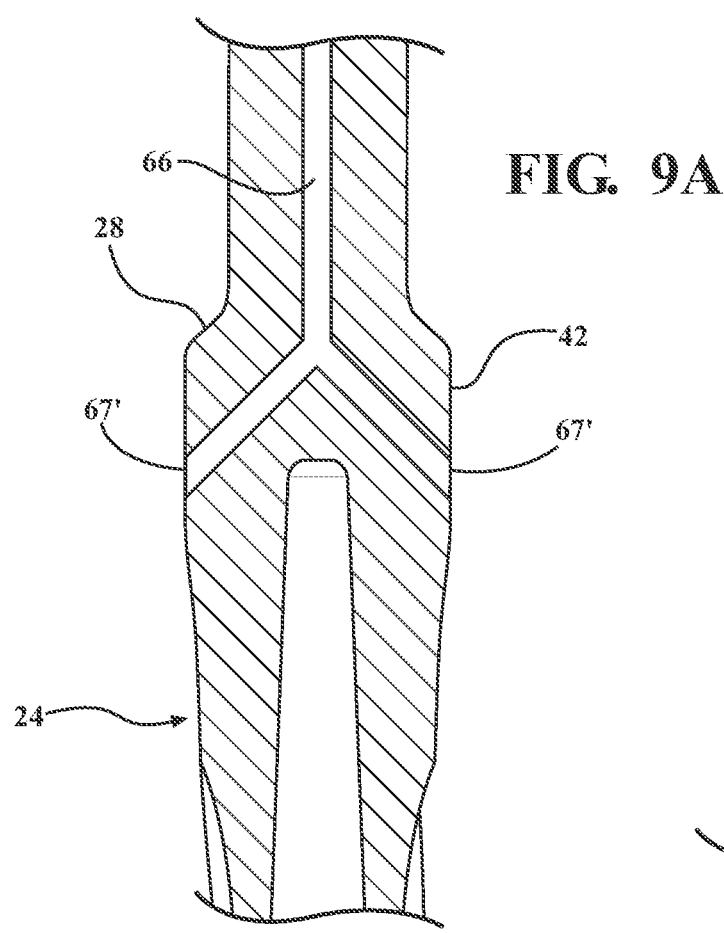
FIGS. 9A and 9B depict alternative embodiments of an irrigated tool like that shown in FIG. 9.
Figure 9B:
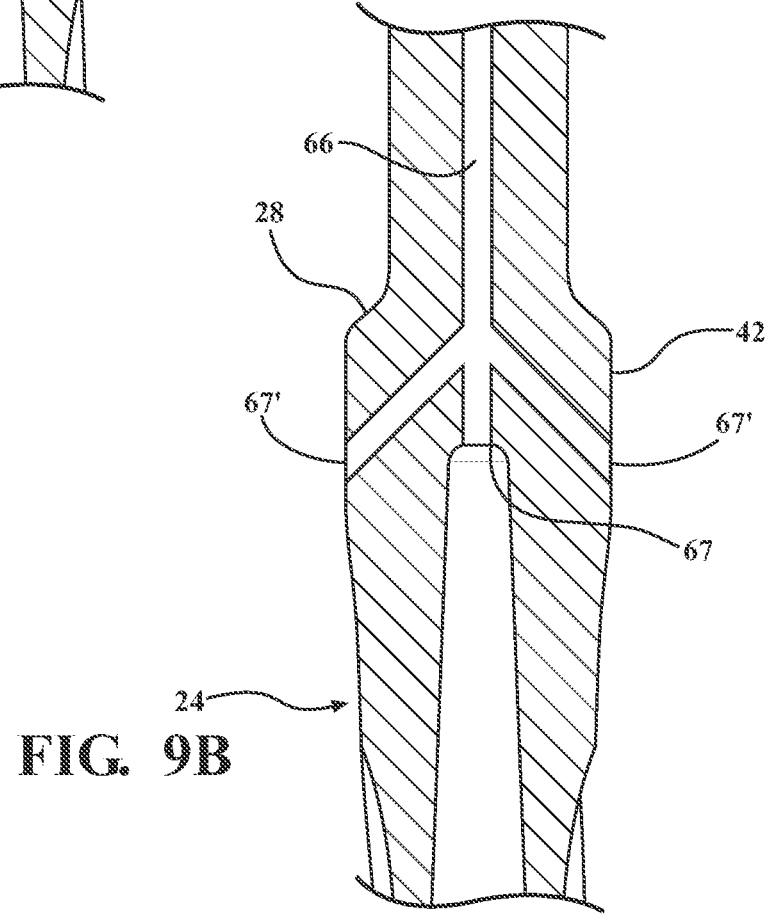

In one contemplated alternative embodiment shown in FIG. 9, the tool 20 is configured with an internal duct 66 to conduct a flow of irrigating fluid longitudinally through the shank 22 to a downstream outlet 67 and/or 67' located at a suitable position on or within the body 24. FIG. 9 shows the outlet 67 as in internal feature discharging directly into the narrow breach end of the cavity 44. In this manner, the irrigation duct 66 is in direct and exclusive fluid communication with the cavity 44. The flow of irrigating fluid will naturally urge debris out of the cavity 44, thus encouraging maximum autografting. In another contemplated embodiment depicted in FIG. 9A, the irrigation duct 66 is routed externally to two or more circumferentially distributed outlets 67' in the stopper section 42 similar to that shown, for example, in PCT/US19/59964 filed Nov. 6, 2019, the entire disclosure of which is incorporated by reference in jurisdictions permitting the practice. In this latter case, the irrigation duct 66 is not in direct fluid communication with the cavity 44. In a still further contemplated embodiment combining both of the preceding designs, which is illustrated in FIG. 9B, the irrigation duct 66 discharges directly into the breach of the cavity 44 through outlet 67, but also includes two or more circumferentially distributed spur outlets 67' like those shown in FIG. 9A. In this third case, fluid pumped through the irrigation duct 66 will concurrently flush the cavity 44 and also wash the external body 24. During post-operative cleaning, the external outlets 67' can be temporarily covered with fingertips or other measures to force all irrigation flow through the internal outlet 67 thereby flushing debris from the cavity 44.

FIG. 10 is a perspective view of a rotary tool 120 according to another embodiment of this invention in which the body 124 is straight-sided (i.e., not tapered). FIG. 11 is a cross-section taken generally along lines 11-11 in FIG. 10. The flutes 132 are shaped with cutting 134 and densifying 136 faces, lands 138 and working edges 140 to provide osseodensification when operated in the densifying mode. The number of flutes 132 is not necessarily correlated to the number of gullets 158 in this embodiment, resulting in only some of the flutes 132 opening directly into a gullet 158. And likewise, only some of the flutes 132 open directly onto a leading flank 150 in this variation of the tool 120.

This rotary tool 120 includes other unique attributes mentioned previously as optional or alternative features. For one, the grinding edges 148 are offset in the densifying direction of rotation. This creates a significantly more aggressive cutting characteristic than the design of FIGS. 1-6. Also, the apex 154 of each grinding edge 148 appears at the radially outmost position. Again, this design cuts more aggressively in the cutting mode than the design of FIGS. 1-6. Another distinguishing feature of the embodiment of FIGS. 10-11 can be seen in the cavity 144, which has straight cylindrical sidewalls to match the outside shape of the body 124. Furthermore, irrigation ducts 166 are integrated into the body 124 of the rotary tool 120 rather than axially through the shank 122 as in FIGS. 9, 9A and 9B. In FIGS. 10-11, the irrigation ducts 166 are formed in the valleys of each flute 132. Those of skill in the art will appreciate other placements, including straight axial designs, circular or oval holes, and the like. In whatever form, the irrigation ducts 166 facilitate externally applied irrigation fluid to enter the cavity 144 in the lateral direction through the body 124. The flow of irrigating fluid through the ducts 166 will naturally urge debris out of the cavity 144, thus encouraging autografting.

The present invention, when operated with a continuous supply of irrigating fluid, may be used to form holes in many different types of materials in addition to bone. For examples, malleable metals, wood and plastics may be used at the host material. The irrigating fluid in these circumstances may be an oil or cutting-fluid substance rather than water or saline. When the non-bone host material is cellular, like in the case of foam metals, wood and some polymers, the host material may behave somewhat like bone. However, when the host material in not cellular but rather solid, displaced stock will have a tendency to mound above and below the hole rather than being auto-grafted into the sidewalls of the hole. This mounding represents malleable material that is plastically displaced by the compression wave of the working edge 40. As a result, the effective stock thickness around a hole formed in non-cellular material will be substantially greater than the original stock thickness, which is considered beneficial to provide greater purchase for an anchor screw.

Advantages of the hollow-point tool 20 of this invention include but are not limited to the following. The torque for use can be as high as 80 ncm for dental applications. Possibly higher for non-dental orthopedic applications. This tool 20 can be used in reverse and act as an osseodensifying bur with easier application and less vertical force as compared with the design of US 2019/0029695. Therefore, the hollow-point shape can be used in all bone preparation applications, including but not limited to socket shield procedures. The tool 20 may have multiple spurs 46 to grind the bone prior to compaction by the working edges 40 in non-cutting rotation. And the cavity 44 contributes positively to reduce the vertical force needed to advance the tool 20 into an osteotomy.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A rotary tool configured to be turned at high speed in both condensing and cutting rotary directions to accomplish different effects while forming a hole in a host material, said rotary tool comprising:
    a shank establishing a longitudinal axis of rotation, said shank being an elongated shaft having an upper end and a lower end,
    a body extending axially from said lower end of said shank, said body having an apical end remote from said shank, a plurality of flutes disposed about said body, each said flute having a cutting face on one side thereof defining a cutting rake angle and a densifying face on the other side thereof defining a densifying rake angle, each said flute having an axial length and a radial depth, each said flute being formed with a continuously negative densifying rake angle along the length thereof, a land formed between each adjacent pair of flutes, each said land having a working edge along said cutting face of one said flute, each said working edge being substantially margin-less,
    a cavity disposed in said body, said cavity extending axially within said body and opening through said apical end, and
    a plurality of spurs disposed on said apical end of said body, said spurs disposed around said opening of said cavity.

2. The rotary tool of claim 1, wherein each said spur has a grinding edge forming a ridgeline between leading and trailing flanks thereof.

3. The rotary tool of claim 2, wherein each said grinding edge has an apex formed at the radially inward most end thereof.

4. The rotary tool of claim 3, wherein each said apex is disposed in a plane that perpendicularly bisects said longitudinal axis.

5. The rotary tool of claim 2, wherein at least one of said spurs has a grinding edge that does not extend along a radial from said longitudinal axis.

6. The rotary tool of claim 2, wherein said grinding edge of each said spur does not extend along a radial from said longitudinal axis.

7. The rotary tool of claim 6, wherein at least one of said spurs is a close-offset spur and at least one of said spurs is a far-offset spur, said grinding edge of said close-offset spur being a short offset from said longitudinal axis and said grinding edge of said far-offset spur being a large offset from said longitudinal axis.

8. The rotary tool of claim 7, wherein each of said short and long offsets is in the cutting direction of rotation.

9. The rotary tool of claim 2, wherein each said trailing flank is truncated by a steep face, a gullet formed between each said steep face and said leading flank of the next adjacent said spur.

10. The rotary tool of claim 9, wherein at least one flute opens directly into one said gullet.

11. The rotary tool of claim 9, wherein at least one flute opens directly onto one said leading flank adjacent an associated said grinding edge.

12. The rotary tool of claim 2, wherein said leading flank is angled relative to said trailing flank by an angular measure comprising an included angle, the included angle between said leading and trailing flanks is between about 45-135 degrees (preferably 90-100 degrees).

13. The rotary tool of claim 12, wherein the included angle is generally equal among said plurality of spurs.

14. The rotary tool of claim 1, wherein said body has an exterior profile comprising a conical taper decreasing from a maximum diameter adjacent said shank to a minimum diameter adjacent said apical end, said cavity has a frusto-conical negative profile that is widest adjacent said apical end and narrowest adjacent said shank, said frusto-conical negative profile having a taper angle generally equal to said conically tapered exterior profile of said body.

15. The rotary tool of claim 1, wherein said cavity has a frusto-conical negative profile that is widest adjacent said apical end and narrowest adjacent said shank.

16. The rotary tool of claim 15, wherein said cavity having an axial length generally equal to the axial length of said flutes along the exterior surface of said body.

17. The rotary tool of claim 1, further including an irrigation duct disposed in said shank, said irrigation duct having a downstream outlet located along said body.

18. The rotary tool of claim 1, wherein said body has an exterior profile selected from the group consisting essentially of: a conical taper decreasing from a maximum diameter adjacent said shank to a minimum diameter adjacent said apical end; and a generally straight profile maintaining a generally constant diameter along the length thereof.

19. The rotary tool of claim 1, wherein each said flute follows a path along said body selected from the group consisting essentially of: a helical spiral; and straight.

20. A rotary tool configured to be turned at high speed in both condensing and cutting rotary directions to accomplish different effects while forming a hole in bone, said rotary tool comprising:

a shank establishing a longitudinal axis of rotation, said shank being an elongated cylindrical shaft having an upper end and a lower end, said shank configured to establish a longitudinal axis of rotation, a drill motor engaging interface formed at said upper end of said shank adapted for connection to a drill motor, an annular locking notch disposed in said shank between said upper and lower ends thereof, a body extending axially from said lower end of said shank, said body having an apical end remote from said shank, said body having a conically tapered exterior profile decreasing from a maximum diameter adjacent said shank to a minimum diameter adjacent said apical end, a plurality of flutes disposed about said body, each said flute having a cutting face on one side thereof defining a cutting rake angle and a densifying face on the other side thereof defining a densifying rake angle, said flutes each having an axial length and a radial depth, each said flute spiraling helically about said body, a stopper section of said body disposed between said flutes and said shank, a land formed between each adjacent pair of said flutes, each said land having a working edge along said cutting face of the one adjacent said flute, each said working edge being substantially margin-less, said working edge helically twisting about said body, said working edges each winding about said body in a direction that turns away from a non-cutting direction as said conically tapered profile decreases in diameter, a cavity disposed in said body, said cavity extending axially within said body and opening through said apical end, said cavity has a frusto-conical negative profile that is widest adjacent said apical end and narrowest adjacent said shank, a plurality of spurs disposed on said apical end of said body, said spurs disposed around said opening of said cavity, each said spur having a grinding edge forming a ridgeline between leading and trailing flanks thereof, the included angle between said leading and trailing flanks being between about 45-135 degrees, each said trailing flank being truncated by a steep face, a gullet formed between each said steep face and said leading flank of the next adjacent said spur, at least one of said spurs being a close-offset spur and at least one of said spurs being a far-offset spur, said grinding edge of said close-offset spur being a short offset from said longitudinal axis and said grinding edge of said far-offset spur being a large offset from said longitudinal axis, each of said short and long offsets being in the cutting direction of rotation, and at least one said flute opening directly into one said gullet, at least one said flute opening directly onto one leading flank adjacent an associated said grinding edge.

* * * * *